(12) United States Patent
Dittmer

(10) Patent No.: US 6,927,918 B2
(45) Date of Patent: Aug. 9, 2005

(54) SURGICAL HEAD CAMERA

(75) Inventor: John Dittmer, Baulkham Hills (AU)

(73) Assignee: The Royal Alexandra Hospital for Children, New South Wales (AU)

( * ) Notice: Subject to any disclaimer, the term of this patent is extended or adjusted under 35 U.S.C. 154(b) by 60 days.

(21) Appl. No.: 10/362,206

(22) PCT Filed: Aug. 13, 2001

(86) PCT No.: PCT/AU01/00989
§ 371 (c)(1), (2), (4) Date: Jun. 2, 2003

(87) PCT Pub. No.: WO02/17014
PCT Pub. Date: Feb. 28, 2002

(65) Prior Publication Data
US 2004/0012713 A1 Jan. 22, 2004

(30) Foreign Application Priority Data
Aug. 23, 2000 (AU) .............................................. PQ9628

(51) Int. Cl.⁷ .......................... G02B 27/14; G09G 5/00; H04N 13/02; H04N 7/18; A61B 3/14
(52) U.S. Cl. ....................... 359/630; 359/631; 359/629; 345/7; 345/8; 348/46; 348/78; 348/77; 348/207.99; 351/206
(58) Field of Search ................................. 359/630, 631, 359/629, 411, 473, 412, 363; 345/7, 8, 9, 87, 102; 348/77, 46, 207.99, 211.4, 376, 78; 351/206

(56) References Cited

U.S. PATENT DOCUMENTS 3,542,457 A * 11/1970 Ziegler et al. .............. 351/206
3,919,475 A    11/1975 Dukich et al.
4,018,514 A *  4/1977 Plummer .................... 351/206
4,621,283 A    11/1986 Feinbloom
5,652,676 A     7/1997 Grinblat
5,803,905 A     9/1998 Allred et al.
5,973,728 A    10/1999 Levitan
6,008,780 A * 12/1999 Clarke et al. .................. 345/8
6,046,712 A *  4/2000 Beller et al. ................... 345/8
6,580,448 B1 * 6/2003 Stuttler ........................ 348/46

FOREIGN PATENT DOCUMENTS

WO    WO 98/20277    5/1998

* cited by examiner

Primary Examiner—Loha Ben
(74) Attorney, Agent, or Firm—Carol M. LaSalle; Bozicevic, Field & Francis LLP

(57) ABSTRACT

An optical system (10) comprises a camera (11) having an imaging means that in use faces downwardly, and an optical assembly. The optical assembly includes a support (14) that extends outwardly from the camera (11) and which has a lumen therethrough to allow transmission of light through the support (14) to the imaging means of the camera (11). The assembly further includes an optical unit (16) mountable to the support (14) and movable relative thereto towards and away from the imaging means of the camera (11). The optical unit (16) includes at least one lens (17) and a mirror assembly ( 22, 23) adapted to reflect at least some light entering the unit (16) that is at approximately a right angle to the orientation of the camera (11), through the lens (17) and into the lumen of the support (14) to the imaging means. The system (10) can be mounted to a headpiece worn by a user, such as a surgeon.

17 Claims, 3 Drawing Sheets

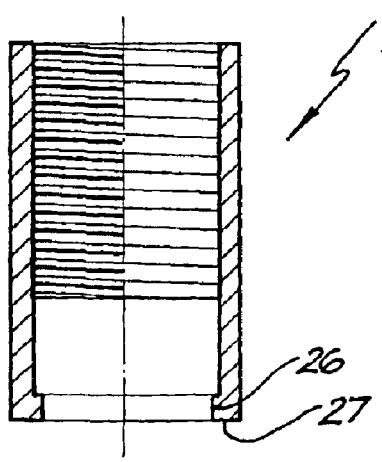
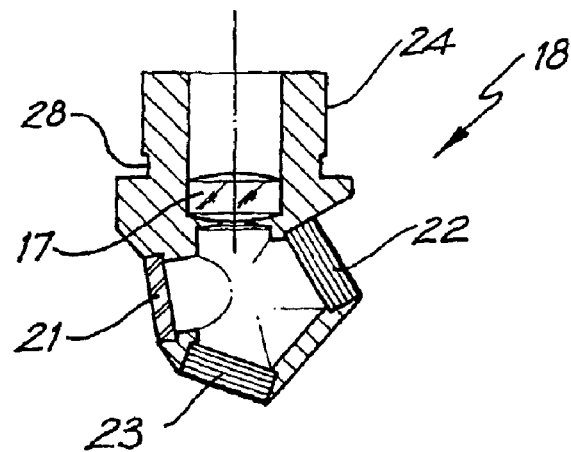
FIG. 3a    FIG. 3b
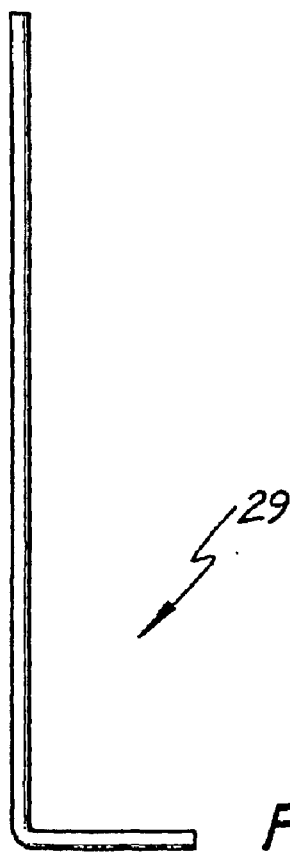
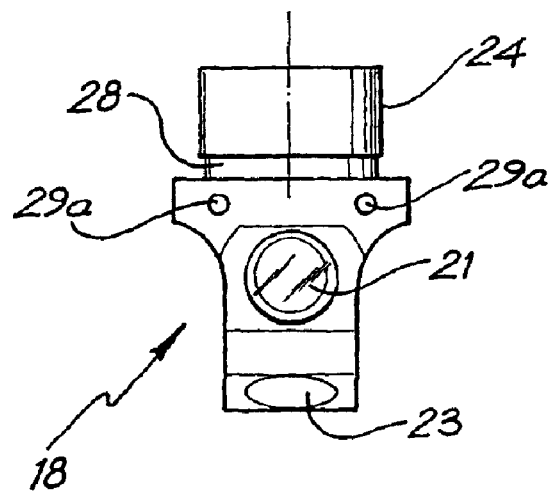
FIG. 3c
FIG. 3d

SURGICAL HEAD CAMERA

FIELD OF THE INVENTION

The present invention relates to an optical system for use in applications, such as surgery, and a device that allows ready and precise adjustment of an optical system when mounted on the head of a user, such as a surgeon.

BACKGROUND OF THE INVENTION

During surgery, it is now common for surgeons to wear a head-mounted video camera positioned in front of the forehead of the surgeon. Such a camera is preferably positioned to image the surgical field. The provision of the camera has a number of advantages. Firstly, it allows others in the surgical team to follow the progress of the surgery on a video screen rather than having to crowd closely about the surgeon to obtain a clear view of the surgical site. This can be particularly advantageous where the surgery is being performed on the small body of a child. By being able to follow the surgery on a video screen, surgical assistants and theatre staff can also be aware of when they are required to take action without crowding the surgeon or blocking the illuminated surgical area.

Recordal of the surgery is also useful if the surgeon wishes to retain a record of the surgical procedure. Video records of such surgery can be particularly useful as an educational tool and for providing an unambiguous record of the actions taken by the surgeon.

One disadvantage of video recordal is the weight and bulkiness of the camera that must be worn by the surgeon. Given that many surgical procedures can last many hours, the necessity of carrying a relatively heavy camera on the forehead can lead to fatigue and neck and back strain for the surgeon. The position of the camera on the forehead also serves to provide a video image that is offset from the actual field of view of the surgeon. This can occasionally result in the camera not being able to image the actual surgical site being operated upon by the surgeon. This is typically compensated by use of a camera with a wide field of view. This in turn, however, has the disadvantage that fine detail in the imaged view of the surgery is lost.

The present invention is directed to an optical system adapted to address some of the problems of existing systems.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention before the priority date of each claim of this application.

SUMMARY OF THE INVENTION

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

According to a first aspect, the present invention is an optical system including a camera having an imaging means, and an optical assembly, the optical assembly including a support means extending outwardly from the camera, the support means defining a lumen therethrough to allow transmission of light through the support means to the imaging means, and an optical unit mounted to the support means and movable relative thereto towards and away from the imaging means, the optical unit including at least one lens and a mirror assembly adapted to reflect at least some light entering the unit through the at least one lens of the unit and the lumen of the support means to the imaging means.

According to a second aspect, the present invention is an optical assembly for a camera, the assembly including a support means mountable forwardly of an imaging means of a camera and defining a lumen therethrough and an optical unit mounted to the support means and movable relative thereto, the optical unit including at least one lens and a mirror assembly adapted to reflect light entering the unit through the at least one lens of the unit and into the lumen of the support means.

In a preferred embodiment, the camera is a compact camera. The camera is preferably a video camera, however, it is envisaged that the invention could be utilised with other camera types. The imaging means can comprise a charge coupled device (CCD). The camera is preferably mounted in a cylindrical tube. The camera preferably has a signal output that allows transmission of the video image to a video screen and/or a video recordal device, such as a video cassette recorder or DVD. The tube in turn can be supported in a bracket. The bracket can be mounted to a headpiece to allow the camera to be worn on the head of a user. In a preferred embodiment, the headpiece, bracket and camera are mounted such that the camera can be positioned between the eyes of a user over the bridge of the nose. In a particularly preferred embodiment, the camera can be used to image an operation area being operated upon by a surgeon or other theatre staff.

The support means preferably comprises a tube mountable on the camera and extending outwardly to an outer edge. The tube preferably has a longitudinal axis and can comprise a relatively thin-walled cylinder. The lumen of the tube is preferably centrally positioned within the tube. The support means can be integrally mounted to the camera or can be removably mounted thereto. The support means preferably incorporates an engagement means adapted to engage with a complementary engagement means on the optical unit. The engagement means of the support means can comprise a screw thread adapted to engage with a complementary screw thread on the optical unit. In one embodiment, the screw thread is on the outer surface of the support means.

In a preferred embodiment, the optical unit preferably includes a window to allow light to enter the unit. The unit is preferably mounted such that the window faces in a direction transverse to the longitudinal axis of the support means. Light entering the window of the unit is preferably reflected by a first mirror in the mirror assembly that is positioned on a side of the unit distal the window. The first mirror is preferably positioned and aligned such that light from the first mirror is reflected towards a second mirror positioned on the inner surface of the unit adjacent its window. The second mirror in turn is positioned and aligned to reflect light received from the first mirror through the lens and into the lumen of the support means. The lens of the unit is preferably a doublet comprising a double convex lens with a convex concave lens cemented thereto. Other suitable constructions for the lens of the unit can be envisaged. It can also be envisaged that the unit may include more than one lens. The unit preferably includes a holding member extending from the base of the unit. The holding member preferably comprises an integral cylindrical tube and is adapted to be engaged with a rotatable sleeve as is defined below. The cylindrical holding member preferably also surrounds and retains the lens in position in the optical unit. A locking ring can be threadedly engaged with the cylindrical member to hold the lens in position.

When mounted on a user, such as a surgeon, the imaging means of the camera preferably faces downwardly while the window of the optical unit faces forwardly relative to the user, such as a surgeon. Indeed, it is preferred that the direction of view of the window be substantially similar to the direction of view of the user, such as a surgeon, when looking straight ahead. Light entering the window of the unit is reflected by the mirror assembly through the lumen and onto the imaging means of the video camera.

The complementary engagement means of the optical unit is preferably a screw thread formed on the inner surface of a sleeve. The sleeve is preferably adapted to relatively rotate about the support means. As the sleeve is rotated about the support means it moves relative to the support means towards or away from the imaging means of the camera. The sleeve preferably comprises a cylindrical tube having a first inner edge and a second outer edge. Such movement of the optical unit relatively towards and away from the imaging means of the camera serves to allow ready adjustment of the focus of the camera whilst still allowing the camera to be relatively lightweight and compact and so positionable between the eyes of the user, such as a surgeon, in normal use.

The holding member of the optical unit is preferably engaged with the sleeve. Preferably, a rim formed on the inner surface of the sleeve at or adjacent its outer edge is adapted to snap into a recess formed in the holding member at or adjacent its connection with the optical unit. While the holding member and sleeve can be so engaged, the sleeve can rotate relative to the holding member, and hence the optical unit, in normal use. Indeed, in normal operation, the alignment of the window of the optical unit relative to the longitudinal axis of the sleeve preferably does not change despite rotation of the sleeve causing it and the optical unit to move longitudinally relative to the support means.

A constraining device preferably extends from the optical unit to the camera or a structure associated therewith. The constraining device, when in position, serves to prevent rotation of the optical unit about the longitudinal axis of the support means on longitudinal movement of the sleeve and optical unit relative to the support means. The constraining device can comprise a wire removably slidably held at one end within a bore formed in the structure of the optical unit. The wire at its other end can be removably slidably held in a bore formed within the camera or a bracket supporting the camera. As the sleeve and optical unit are moved relative to the support means, the wire preferably slides within the bore formed in the camera or bracket. The bore in the optical unit is preferably at right angles to the bore in the bracket thereby requiring that the wire have a right angled turn adjacent its end slidably held within the optical unit. The wire can be formed from stainless steel or other suitable material. If the optical unit needs to be removed from the support means, the wire is preferably slid from the bore in the camera or bracket and then slid from the bore in the optical unit.

According to a further aspect, the present invention is a position adjustment device for an optical system, the device including a base member, an arm extending outwardly from the base member to a distal end, the arm being pivotally mounted to the base member and adapted to pivot relatively thereto in a first plane of movement, and a bracket means pivotally mounted to the distal end of the arm and adapted to pivot relative to the arm in a second plane of movement that is transverse to that of the first plane of movement.

In a preferred embodiment, the device is adapted for use with an optical system comprising a camera and/or a light source. The camera and/or light source are preferably for use by surgeons or other surgical theatre staff. It will be appreciated, however, that the camera and/or light source could be used for other applications.

When used by a surgeon, the base member of the device is preferably mounted to a head support member worn by the surgeon. The head support member can comprise a cap-like member having a strap extending about the head proximate the forehead of the surgeon. The base member is preferably mounted to the strap such that the adjustment device is normally mounted forwardly of the forehead and over the bridge of the nose of the surgeon.

The pivotal movement of the arm relative to the base member is preferably provided by a pivot mounting. The pivot mounting can comprise a pivot pin mounted in the arm and rotatable relative to the base member. When the device is in use, the pivot pin is preferably substantially vertical. This substantially vertical orientation allows the arm to pivot from side to side relative to the base member.

Control of the pivotal movement is preferably provided by a control means. The control means preferably comprises a shaft member having an external thread formed thereon. The thread preferably extends from a first end to a second end distal the first end. The second end is preferably mounted to the arm adjacent its pivotal connection with the base member. The second end while connected to the arm can still rotate relative thereto. Extending outwardly from the base member is a first extension member having a threaded ring extending upwardly therefrom. The thread of the threaded ring is complementary to the thread of the control means such that on rotation of the control means, the shaft moves forwardly and backwardly relative to the position of the threaded ring. This movement in turn causes the arm to move relative to the base member. The provision of a knurled knob, having a diameter larger than that of the threaded shaft, at the first end of the threaded shaft serves to allow relatively fine control of the pivotal movement of the arm. The threaded shaft of the control means has the advantage of providing relatively fine control of the pivotal movement while also not allowing movement of the arm unless the shaft is turned.

The arm preferably has a first portion that extends outwardly and downwardly from the base member of the device. The arm further preferably has a second integral portion that extends generally outwardly to the distal end. The second portion preferably has a shorter length than the first portion.

The bracket means is preferably adapted to support an optical system including both a camera and a light source. In one embodiment, the optical system can include the features of the optical system defined above as the first and second aspects of the invention.

The bracket means is pivotally mounted to the distal end of the arm. This pivotal mounting is provided by a pivot pin extending through the distal end of the arm and a support member of the bracket means. When the device is in use, this pivot pin is preferably substantially horizontal. This substantially horizontal orientation allows the bracket means to pivot upwardly and downwardly relative to the distal end of the arm.

Control of the pivotal movement of the bracket means relative to the distal end of the arm is also preferably provided by a control means. The control means again preferably comprises a shaft member having an external thread formed thereon as defined above. The second end of the shaft member is preferably mounted to a second extension member extending downwardly from the bracket means. The second end while connected to the second extension member can still rotate relative thereto. Extending sidewardly from the arm at or adjacent the connection between the first and second portions is a threaded ring. The thread of the threaded ring is complementary to the thread of the control means such that on rotation of the control means, the shaft moves forwardly and backwardly relative to the position of the threaded ring. This movement, in turn, causes the bracket means to move relative to the distal end of the arm. Again, the provision of a larger diameter knurled knob at the first end of the threaded shaft serves to allow relatively fine control of the pivotal movement of the bracket means. The threaded shaft of the control means has the advantage of providing relatively fine control of the pivotal movement while also not allowing movement of the bracket means unless the shaft is turned.

In a preferred embodiment, the pivotal movement of the pivoting mounting between the base member and the arm is at a right angle to the pivotal movement of the bracket means to the distal end of the arm.

The combination of the side to side movement and the up and down movement provided by the respective pivotal mountings serve to allow a surgeon, or more likely a surgical assistant, to readily and precisely adjust the orientation of a camera and light source held in the bracket means during a surgical procedure. This is particularly advantageous as it serves to help to ensure that the camera is always imaging the operation area. It is also important when the camera has a relatively small field of view. This is important where others in the surgical team are relying upon such images so that they can appropriately assist the surgeon during the operation. It also ensures that a good quality video record of the surgery can be more readily made which is useful if the video record is to be later used for educational or other purposes.

BRIEF DESCRIPTION OF THE DRAWINGS

By way of example only, a preferred embodiment of the present invention is now described with reference to the accompanying drawings:

FIGS. 3a–3d provide further views of various components of the optical system depicted in FIGS. 1 and 2;

FIG. 4b is a side elevation view of the position adjustment device of FIG. 4a.

PREFERRED MODE OF CARRYING OUT THE INVENTION

Figures 1, 2:
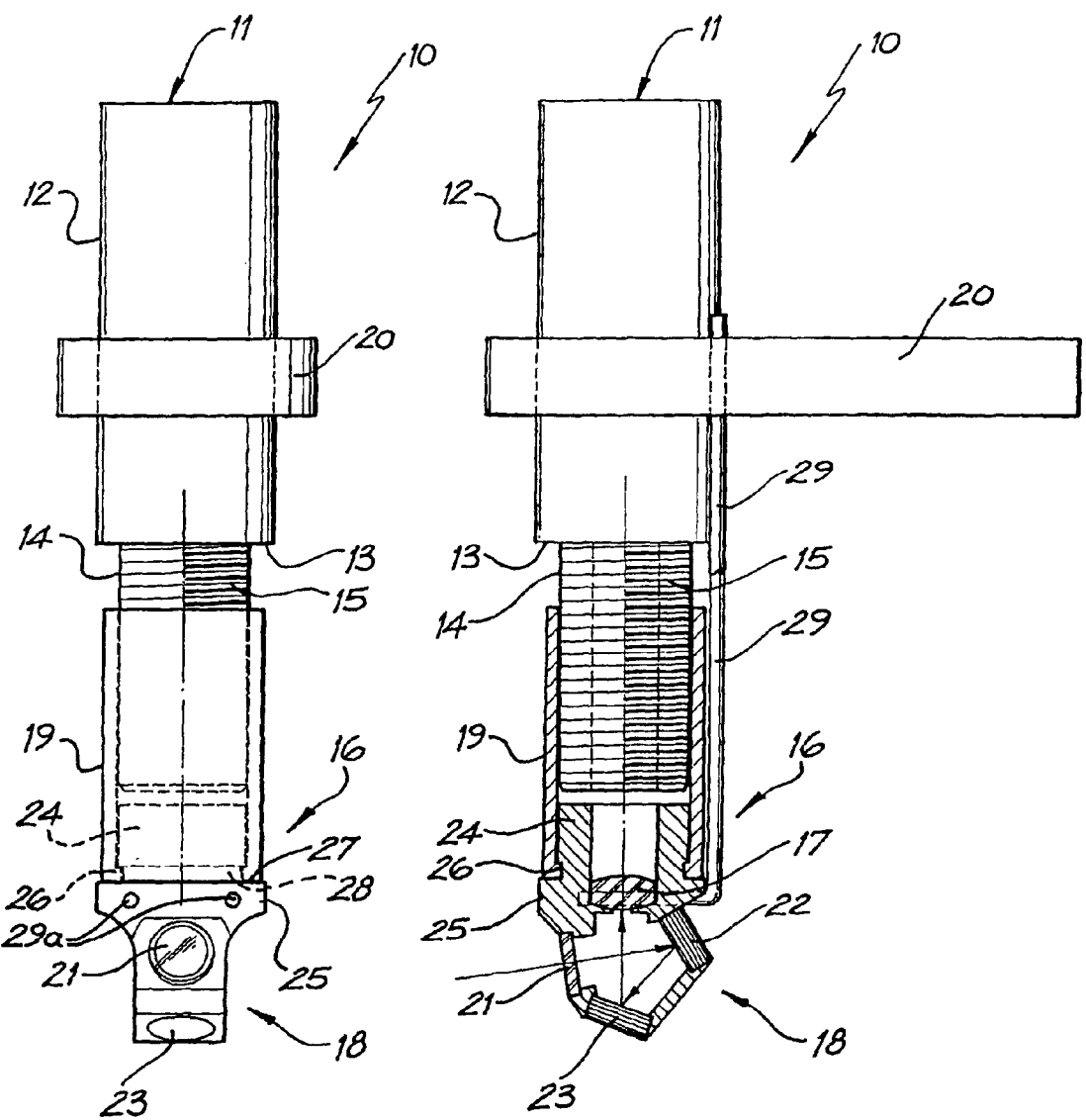
FIG. 1 is a view of the camera and optical system according to one aspect of the present invention.
FIG. 2 is a further view of the camera and optical system of FIG. 1.

An optical system according to one aspect of the present invention is generally depicted as 10 in FIGS. 1 and 2.

Figure 4A:
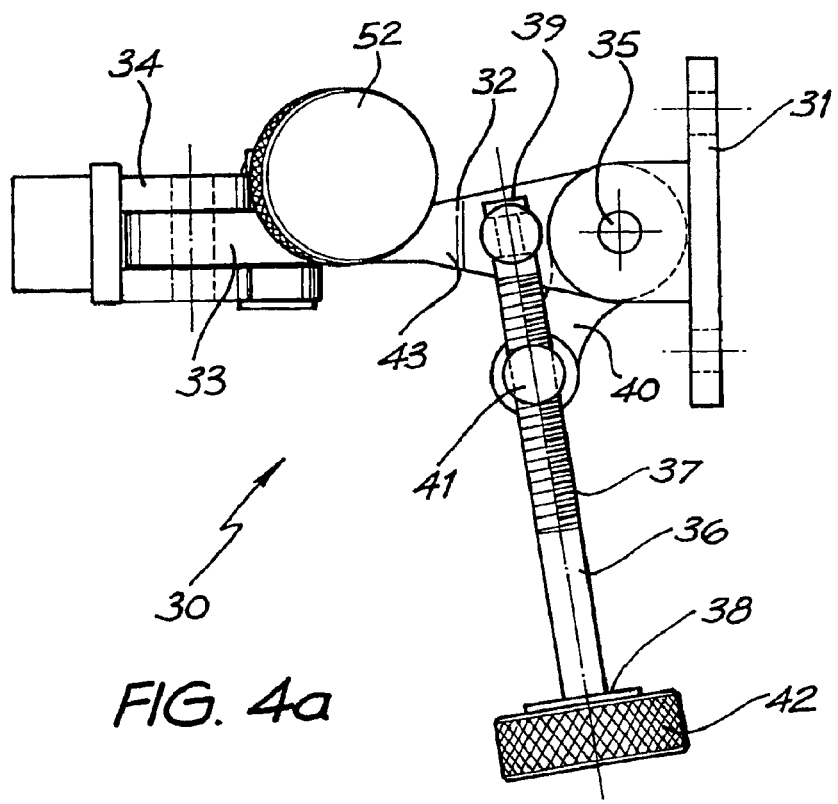
FIG. 4a is a plan view of a position adjustment device for a camera and optical system according to a further aspect of the present invention.
Figure 4B:
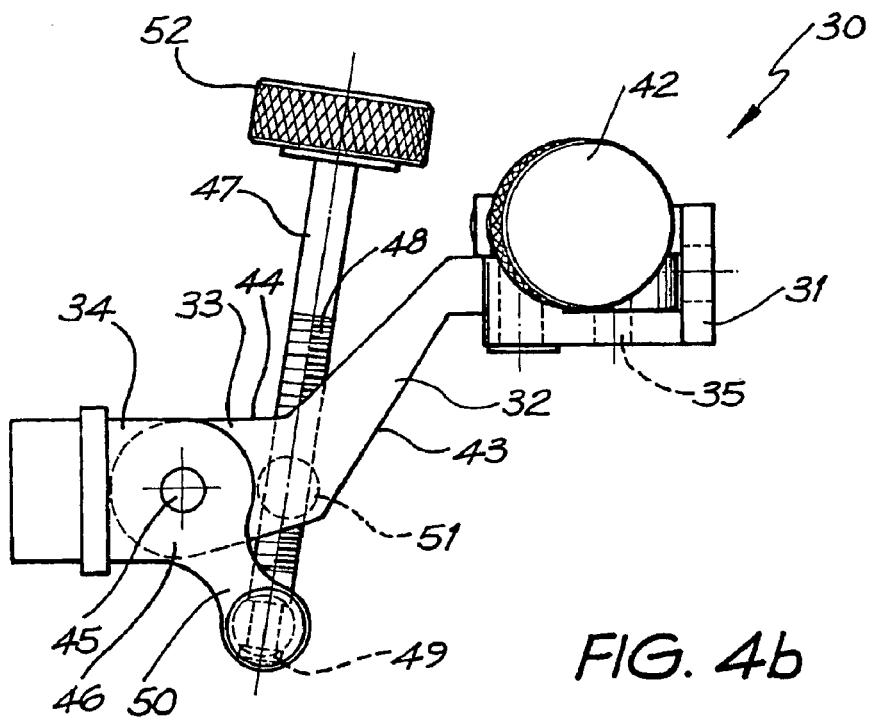

The optical system 10 is adapted to be mounted to a head support worn by a user, such as a surgeon whilst performing a surgical procedure. In one embodiment, the optical system 10 can be mounted to a position adjustment device 30 as is depicted in FIGS. 4a and 4b and which is described in more detail below.

The optical system 10 comprises a compact "lipstick" style of camera 11 positioned within a cylindrical tube 12. An example of one suitable type of compact camera is the Sony™ DXC-LS1P video camera. The camera has a signal output that allows transmission of the video image to a video screen an/or a video recordal device, such as a video cassette recorder or DVD (not depicted). The cylindrical tube 12 is in turn supported in a bracket 20. The bracket 20 can be mounted to a headpiece to allow the camera to be worn on the head of a user, such as a surgeon.

Extending forwardly from the front edge 13 of the camera 11 is a cylindrical support 14 having a longitudinal axis and a central lumen extending therethrough. In the depicted embodiment, the support 14 is integrally formed with the front edge 13 of the camera 11. Light entering the support 14 can travel through the lumen to the charge coupled device (CCD) within the camera 11. The outer surface of the support 14 has a screw thread 15, the purpose of which is described below.

Mounted to the support 14 is an optical unit 16. The optical unit 16 includes a lens 17, a mirror assembly 18 and a sleeve 19. The sleeve 19 comprises a substantially cylindrical tube having a screw thread on its inner surface that is complementary to the screw thread 15 on the support 14.

The optical unit 16 includes a window 21 to allow light to enter the unit. The optical unit 16 is mounted such that the window 21 faces in a direction transverse to the longitudinal axis of the support 14. Light entering the window 21 of the optical unit 16 is reflected by a first mirror 22 in the unit 16 that is positioned on a side of the unit 16 distal the window 21. The first mirror 22 is positioned and aligned such that light from the first mirror 22 is reflected towards a second mirror 23 positioned on the inner surface of the unit 16 adjacent the window 21. The second mirror 23 in turn is positioned and aligned to reflect light received from the first mirror 22 through the lens 17 and into the lumen of the support 14. The lens 17 of the unit 16 is a doublet comprising a double convex lens with a convex concave lens cemented thereto (Edmund Industrial Optics, Barrington, N.J., USA). Other suitable constructions for the lens of the unit 16 can be envisaged. It can also be envisaged that the unit 16 may include more than one lens.

The unit 16 further includes an integral cylindrical holding member 24 extending from the base 25 of the unit 16. The holding member 24 is adapted to engage with the sleeve 19. The cylindrical holding member 24 also surrounds and retains the lens 17 in position in the optical unit 16. A locking ring that is threadedly engaged with the cylindrical member 24 is used to hold the lens 17 in position.

When mounted on a user, such as a surgeon, the camera preferably faces downwardly while the window 21 of the unit 16 faces forwardly relative to the surgeon. Indeed, it is preferred that the direction of view of the window 21 be substantially similar to the direction of view of the surgeon when looking straight ahead. Light entering the window 21 of the unit 16 is reflected by the combination of the first mirror 22 and the second mirror 23 through the lumen and into the camera 11.

The sleeve 19 is adapted to relatively rotate about the support 14. As the sleeve 19 is rotated about the support 14 it moves relative to the support 14 towards or away from the camera 11. Movement of the unit 16 relatively towards and away from the camera 11 serves to allow ready adjustment of the focus of the camera 11 whilst still allowing the camera 11 to be relatively lightweight and compact and so positionable between the eyes of the surgeon in normal use.

The holding member 24 of the unit 16 is engaged with the sleeve 19. A rim 26 formed on the inner surface of the sleeve 19 at or adjacent its outer edge 27 is adapted to snap into a recess 28 formed in the holding member 24 at or adjacent its connection with the unit 16. While the holding member 24 and sleeve 19 can be so engaged, the sleeve 19 can still rotate relative to the holding member 24, and hence the unit 16, in normal use. Indeed, in normal operation, the alignment of the window 21 of the unit 16 relative to the longitudinal axis of the sleeve 19 does not change despite rotation of the sleeve 19 causing it and the unit 16 to move longitudinally relative to the support 14.

A constraining device, comprising a stainless steel wire 29, extends from the unit 16 to the bracket 20. The wire 29, when in position, serves to prevent rotation of the unit 16 about the longitudinal axis of the support 14 on longitudinal movement of the sleeve 19 and unit 16 relative to the support 14. The wire 29 is removably slidably held at one end within a bore 29a formed in the structure of the unit 16. The wire 29 at its other end can be removably slidably held in a bore formed within the bracket 20. As the sleeve 19 and unit 16 are moved relative to the support 14, the wire 29 slides within the bore formed in the bracket 20. The alignment of the bore 29a in the unit 16 is preferably at right angles to the bore in the bracket 20 thereby requiring that the wire have a right angled turn adjacent its end slidably held within the unit 16. If the optical unit 16 needs to be removed from the support 14, the wire 29 is slid from the bore in the bracket 20 and then slid from the bore 29a in the unit 16.

In use, the camera 11 is mounted within the bracket 20 before being positioned on the head of a user, such as a surgeon. The mounting of the camera is such that the window 21 of the unit 16 faces forwardly from approximately between the eyes of the user wearing the camera 11. The sleeve 19 can then be rotated relative to the support 14 to adjust the focus of the camera.

One embodiment of a position adjustment device according to the present invention is depicted as 30 in FIGS. 4a and 4b.

This device 30 is adapted to be mounted to a headpiece worn by a user, such as a surgeon performing a surgical procedure. The headpiece can comprise a cap-like member having a strap extending about the head proximate the forehead of the user. The base member is preferably mounted to the strap such that the adjustment device is normally mounted forwardly of the forehead and over the bridge of the nose of the user. The device 30 can be used to support an optical system 10, as described above, and/or a light source.

The device 30 includes a base member 31, an arm 32 extending outwardly from the base member 31 to a distal end 33. The arm 32 is pivotally mounted to the base member 31 and is adapted to pivot relatively thereto in a first plane of movement. A bracket 34 is also pivotally mounted to the distal end 33 of the arm 32 and is adapted to pivot relative to the arm 32 in a second plane of movement that is transverse to that of the first plane of movement.

The pivotal movement of the arm 32 relative to the base member 31 is provided by a pivot pin 35 mounted through the arm 32 and the base member 31. When the device 30 is in use, the pivot pin 35 is preferably substantially vertical. This substantially vertical orientation allows the arm 32 to pivot from side to side relative to the base member 31.

Control of the pivotal movement is provided by a shaft 36 having an external thread 37 formed thereon. The thread 37 extends from a first end 38 to a second end 39 distal the first end 38. The second end 39 is mounted to the arm 32 adjacent the pivot pin 35. The second end 39 while connected to the arm 32 can still rotate relative thereto, Extending outwardly from the base member 31 is an extension member 40 having a threaded ring 41 extending upwardly therefrom. The thread of the threaded ring 41 is complementary to the thread 37 such that on rotation of the shaft 36, the shaft 36 moves forwardly and backwardly relative to the position of the threaded ring 41. This movement in turn causes the arm 32 to move relative to the base member 31. The provision of a knurled knob 42, having a diameter larger than that of the threaded shaft 36, at the first end 38 of the threaded shaft serves to allow relatively fine control of the pivotal movement of the arm 32. Use of the threaded shaft 36 has the advantage of providing relatively fine control of the pivotal movement while also not allowing movement of the arm 32 unless the shaft 36 is turned.

The arm 32 has a first portion 43 that, in normal use, extends outwardly and downwardly from the base member 31 and a second integral portion 44 that extends generally outwardly to the distal end 33. The second portion 44 has a shorter length than the first portion 43.

The bracket 34 is pivotally mounted to the distal end 33 of the arm 32. This pivotal mounting is provided by a pivot pin 45 extending through the distal end 33 of the arm 32 and a support member 46 of the bracket 34. When the device 30 is in use, this pivot pin 45 is normally substantially horizontal. This substantially horizontal orientation allows the bracket 34 to pivot upwardly and downwardly relative to the distal end 33 of the arm 32.

Control of the pivotal movement of the bracket 34 relative to the distal end 33 of the arm 32 is also provided by a control shaft 47 having an external thread 48 formed thereon. The second end 49 of the shaft 47 is mounted to an extension member 50 extending downwardly from the bracket 34. The second end 49 while connected to the extension member 50 can still rotate relative thereto. Extending sidewardly from the arm 32 at or adjacent the connection between the first and second portions 43,44 is a threaded ring 51. The thread of the threaded ring 51 is complementary to the thread 48, such that rotation of the shaft 47 forwardly and backwardly relative to the position of the threaded ring 51, in turn causes the bracket 34 to move relative to the distal end 33 of the arm 32. Again, the provision of a larger diameter knurled knob 52 at the first end of the threaded shaft 47 serves to allow relatively fine control of the pivotal movement of the bracket 34. The threaded shaft 47 has the advantage of providing relatively fine control of the pivotal movement while also not allowing movement of the bracket 34 unless the shaft 47 is turned by a user.

In the depicted embodiment, the pivotal movement of the arm 32 relative to base member 31 is at a right angle to the pivotal movement of the bracket 34 to the distal end 33 of the arm 32.

The combination of the side to side movement and the up and down movement provided by the respective pivotal mountings serve to allow the wearer, such as a surgeon, or more likely, a surgical assistant, to readily and precisely adjust the orientation of a camera and light source held in the bracket 34 during a surgical procedure. This is particularly advantageous as it serves to help to ensure that the camera is always imaging the operation area. This is important where others in the surgical team are relying upon such images so that they can appropriately assist the surgeon during the operation. It also ensures that a good quality video record of the surgery can be more readily made which is useful if the video record is to be later used for educational or other purposes.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A head-mountable optical assembly for a camera, the assembly comprising: a headpiece adapted to be worn on the head of a user; a bracket mounted to the headpiece for mounting the camera to the headpiece; a support means mountable forwardly of an imaging means of the camera and defining a lumen therethrough; and an optical unit mountable to the support means and movable relative thereto, the optical unit including at least one lens and a mirror assembly adapted to reflect light entering the unit through the at least one lens of the unit and into the lumen of the support means; wherein the headpiece, bracket and support means are adapted to position the optical unit between the eyes of the user when the headpiece is placed on the head of the user.

2. A head-mountable optical assembly of claim 1 wherein the support means comprises a tube mountable on the camera and extending outwardly to an outer edge.

3. A head-mountable optical assembly of claim 2 wherein the support means is integrally mounted to the camera.

4. A head-mountable optical assembly of claim 2 wherein the support means has an outer surface having a screw thread formed therein engageable with a complementary screw thread on the optical unit.

5. A head-mountable optical assembly of claim 4 wherein the optical unit includes a holding member extending from a base of the unit, the holding member comprising an integral cylindrical tube engageable with a rotatable sleeve.

6. A head-mountable optical assembly of claim 5 wherein the complementary screw thread of the optical unit is formed on an inner surface of the sleeve such that the sleeve, on rotation about the support means, moves relative to the support means towards or away from the imaging means of the camera.

7. A head-mountable optical assembly of claim 6 wherein the holding member of the optical unit has a recess at or adjacent its connection with the optical unit that is engageable with a rim formed on the inner surface of the sleeve at or adjacent the sleeve's outer edge, the rim being adapted to snap into the recess formed in the holding member.

8. A head-mountable optical assembly of claim 1 wherein the optical unit has a window to allow light to enter the unit, the window being mounted such that the window faces in a direction transverse to the longitudinal axis of the support means.

9. A head-mountable optical assembly of claim 8 wherein the mirror assembly includes a first mirror positioned on a side of the unit distal the window and a second mirror positioned on an inner surface of the unit adjacent the window, the first mirror being positioned and aligned such that the light from the first mirror is reflected towards the second mirror.

10. A head-mountable optical assembly of claim 9 wherein the second mirror is positioned and aligned to reflect light received from the first mirror through the lens and into the lumen of the support means.

11. A head-mountable optical assembly of claim 1 wherein the lens of the unit is a doublet comprising a double convex lens with a convex concave lens cemented thereto.

12. A head-mountable optical assembly of claim 1 further comprising a constraining device that extends from the optical unit to the camera or a bracket associated therewith and which serves to prevent rotation of the optical unit about the longitudinal axis of the support means on longitudinal movement of the optical unit relative to the support means.

13. A head-mountable optical assembly of claim 12 wherein the constraining device comprises a wire removably slidably held at or adjacent one end within a bore formed in the structure of the optical unit and removably slidably held at or adjacent its other end in a bore formed within the camera or the bracket supporting the camera, such that on relative movement of the optical unit to the support means, the wire slides within the bore formed in the camera or bracket.

14. A head-mountable optical system comprising: a camera having an imaging means; and an optical assembly, the optical assembly comprising: a headpiece adapted to be worn on the head of a user; a bracket mounted to the headpiece for mounting the camera to the headpiece; a support means extending outwardly from the camera and defining a lumen therethrough to allow transmission of light through the support means to the imaging means; and an optical unit mountable to the support means and movable relative thereto towards and away from the imaging means, the optical unit including at least one lens and a mirror assembly adapted to reflect at least some light entering the unit through the at least one lens of the unit and the lumen of the support means to the imaging means; wherein the headpiece, bracket and support means are adapted to position the optical unit between the eyes of the user when the headpiece is placed on the head of the user.

15. A head-mountable optical system of claim 14 wherein the camera is a compact video camera.

16. A head-mountable optical system of claim 15 wherein the imaging means is a charge coupled device (CCD).

17. A head-mountable optical system comprising: a camera having an imaging means; an optical assembly comprising: a headpiece adapted to be worn on the head of a user; a bracket mounted to the headpiece for mounting the camera to the headpiece; a support means extending outwardly from the camera and defining a lumen therethrough to allow transmission of light through the support means to the imaging means; and an optical unit mountable to the support means and movable relative thereto towards and away from the imaging means, the optical unit including at least one lens and a mirror assembly adapted to reflect at least some light entering the unit through the at least one lens of the unit and the lumen of the support means to the imaging means; and a position adjustment device including: a base member; an arm extending outwardly from the base member to a distal end, the arm being pivotally mounted to the base member and adapted to pivot relatively thereto in a first plane of movement; and a bracket means for the camera pivotally mounted to the distal end of the arm and adapted to pivot relative to the arm in a second plane of movement that is transverse to that of the first plane of movement; wherein the headpiece, bracket and support means are adapted to position the optical unit between the eyes of the user when the headpiece is placed on the head of the user.

* * * * *